United States Patent [19]
Deroux et al.

[11] Patent Number: 5,273,678
[45] Date of Patent: Dec. 28, 1993

[54] STABLE SOLUTION OF SODIUM HYPOCHLORITE

[75] Inventors: Jean Deroux, Dammarie les Lys; Maël Le Rat, Yerres; Jean-Paul Compagnon, Dammarie les Lys, all of France

[73] Assignee: Cooperation Pharmaceutique Francaise, Melun, France

[21] Appl. No.: 734,595

[22] Filed: Jul. 23, 1991

[30] Foreign Application Priority Data

Aug. 9, 1990 [EP] European Pat. Off. ........ 90402276.1

[51] Int. Cl.⁵ .................... C01B 11/06; A01N 59/08
[52] U.S. Cl. .................. 252/187.26; 252/187.24; 252/187.25; 424/661
[58] Field of Search .................. 252/187.26, 187.25

[56] References Cited

U.S. PATENT DOCUMENTS 4,337,163  6/1982  Schilp.
4,898,681  2/1990  Burton.

FOREIGN PATENT DOCUMENTS 590112   8/1988  Australia.
2593704  4/1987  France.
2021947  3/1979  United Kingdom.

Primary Examiner—Robert L. Stoll
Assistant Examiner—Joseph D. Anthony
Attorney, Agent, or Firm—Webb, Burden, Ziesenheim & Webb

[57] ABSTRACT

The present invention relates to a stable solution of sodium hypochlorite which is useful as an antiseptic. The solution contains sodium hypochlorite in a quantity sufficient for 4 to 6 grams per liter of active chlorine, a pH regulator in a quantity sufficient to yield a pH greater than 10 and less than or equal to 10.5 and purified water in a quantity sufficient to yield 1 liter of solution.

8 Claims, 1 Drawing Sheet

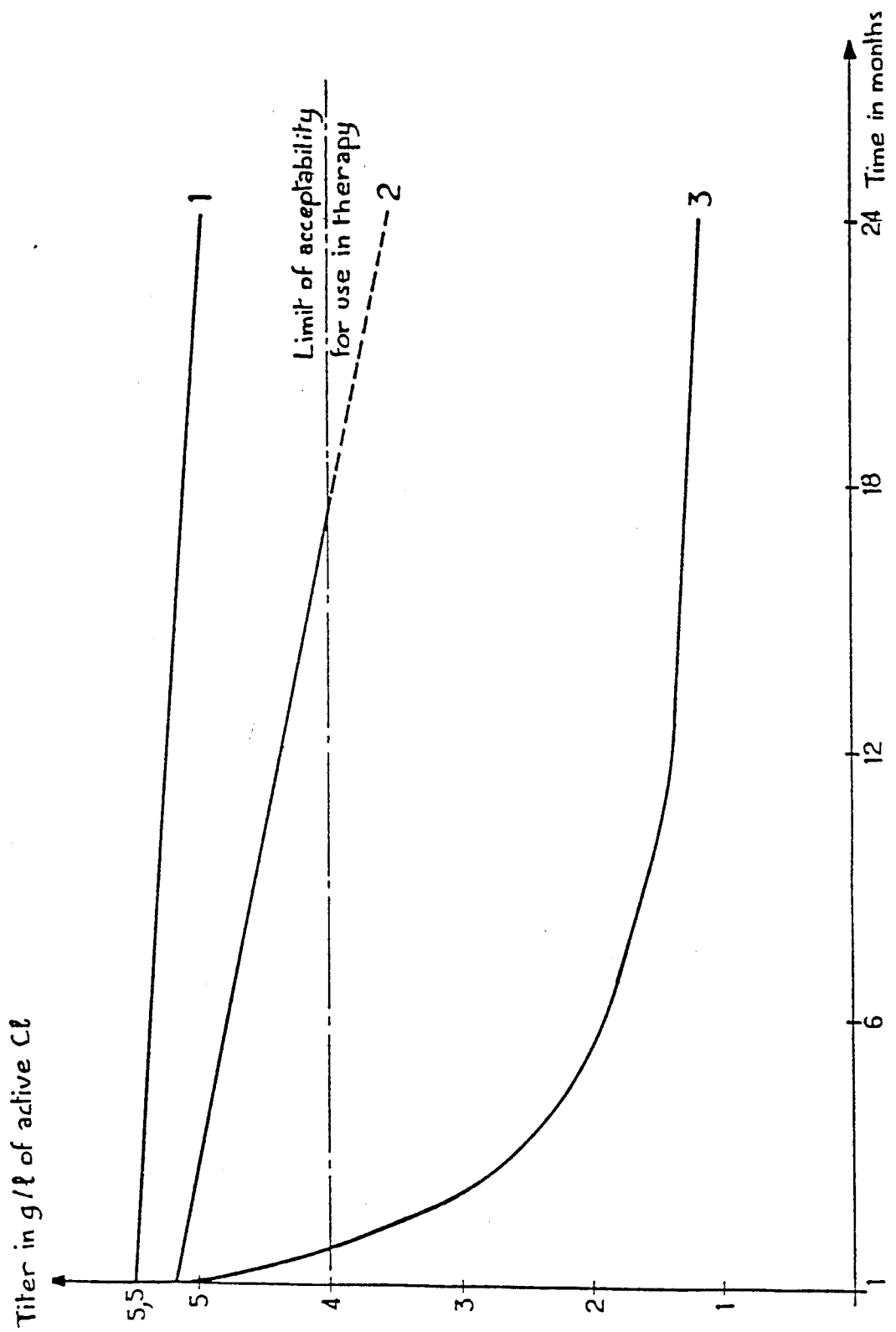

STABLE SOLUTION OF SODIUM HYPOCHLORITE

BACKGROUND OF THE INVENTION

1. Field of the Invention

The present invention relates to a novel solution of sodium hypochlorite, namely a stable solution of this product which is suitable as an antiseptic.

2. Prior Art

Sodium hypochlorite solution has been used for its bactericidal properties since the beginning of the 19th century (in particular since the work of LABARRAQUE in about 1820). In 1914, for use in the washing of war wounds, DAKIN found it necessary to neutralize the excess alkalinity of the solution in order to reduce its irritant action. For this neutralization, he used boric acid at a rate of about 4 g per liter. DAUFRESNE subsequently replaced the boric acid with sodium bicarbonate, but it is the so-called VAL de GRACE formulation published in about 1930 which was entered in the pharmacopeia under the name of DAKIN's solution.

Neutral dilute sodium hypochlorite solution (DAKIN's solution) is entered in the French Pharmacopeia, 10th edition, January 1989, under the following formulation:

monosodium carbonate: 15 g
Javelle water, in a quantity sufficient to yeild: 5 g of active chlorine
potassium permanganate: 0.01 g
cold boiled water in a quantity sufficient to yield a 1000 ml solution As sodium hypochlorite decomposes rapidly to release chlorine, it is specified in said pharmacopeia that this solution must be stored for a maximum of fifteen days in stoppered containers, in a cool place at a temperature below 15° C. and protected from the light. The lower limit of active chlorine accepted for the solution is 4 g of active chlorine per liter.

A time limit as short as this makes it very difficult to utilize this product industrially.

Through the development of very particular manufacturing conditions, excluding especially the presence of metal particles, it has been possible to obtain a solution with a time limit corresponding to D+14, D being the day of acceptance by the control services [q.v. Ann. Pharmaceutiques Françaises 1984, 42, No. 5, pp. 417-423].

In his thesis presented to the Faculty of Pharmacy in Dijon on Feb. 16, 1987, J. F. LAHET concluded that the instability of DAKIN's solution at room temperature is a reality and still limits its use.

In patent FR 2 593 704, the Applicant described a dilute solution of sodium hypochlorite stabilized with monosodium phosphate, which has the following composition:

sodium hypochlorite in a quantity sufficient to yield 5 g of active chlorine
monosodium phosphate in a quantity sufficient to yield a pH of 9.6 to 10
purified water in a quantity sufficient to yield a 1 liter solution The monosodium phosphate must be used in a sufficient amount to give the sodium hypochlorite solution a pH of between 9.6 and 10 and preferably of between 9.7 and 9.9. This pH range makes it possible to achieve a stability of about six months or more.

This hypochlorite solution can also contain any type of coloring substance which is inert towards the hypochlorite and the monosodium phosphate. This substance can advantageously be potassium permanganate, as in DAKIN's solution.

However, it has proved necessary to continue researching in order to obtain a sodium hypochlorite solution with a longer storage time.

SUMMARY OF THE INVENTION

It has been found, totally surprisingly, that a sodium hypochlorite solution having an active chlorine titer of between 4 and 6 g/l and a pH which is greater than 10, between 10 and 10.5 and preferably about 10.25 can be stored for at least 24 months.

The teachings of the prior art did not make it possible to predict that such a composition would be both stable and effective as an antiseptic.

In fact, chlorine is known to be a very effective antimicrobial and antiviral agent, its active form being hypochlorous acid, which is advantageously used in aqueous solution if the pH is acid.

It is known that the maximum activity of such a solution is obtained at pH 5, whereas, in a more acid medium, volatile chlorine is formed which causes the solution to lose part of its activity. In this respect, reference may be made to the work by A. CREMIEUX entitled "LES ANTISEPTIQUES", Base microbiologique de leur utilisation ("ANTISEPTICS", Microbiological basis for their use), Edition Sarget, Mérignac, 1982, and to the work by A. DAUPHIN entitled "HYGIENE HOSPITALIERE PRATIQUE" ("PRACTICAL HOSPITAL HYGIENE"), Editions Mddicales Internationales, Paris, 1985.

In an alkaline medium, the stability of such solutions is still assured, but the antimicrobial activity is much lower (the journal Prescrire July-August 1990, volume 10, No. 98).

Hitherto, it has therefore been very difficult, if not impossible, to find an acceptable compromise between stability on the one hand and efficacy on the other.

The sodium hypochlorite solution of the invention makes it possible to overcome the disadvantages of the prior art and therefore to have a solution which can be produced industrially and is stable for at least 24 months, and whose therapeutic efficacy is improved compared with the conventional DAKIN's solution or with the solution according to patent FR 2 593 704.

BRIEF DESCRIPTION OF THE DRAWINGS

The FIGURE illustrates the stability with respect to time of the solution of the present invention, kept at 20°-25° C., as compared with that of the solution according to French Patent No. 2,593,704 and DAKIN's solution.

DETAILED DESCRIPTION OF THE PREFERRED EMBODIMENTS

The invention relates to a sodium hypochlorite solution which has the following composition:

sodium hypochlorite in a quantity sufficient to yield 4 to 6 g/l of active chlorine
pH regulator in a quantity sufficient for $10 < pH \cong 10.5$
purified water in a quantity sufficient to yield a 1 liter solution The concentration of sodium hypochlorite in the solution according to the invention must meet the prescribed requirements applicable in human therapy.

A concentration of 4 g/l of hypochlorite is the minimum needed to meet the requirements of the French Pharmacopeia (10th edition, 1989) and a concentration of 6 g/l of hypochlorite corresponds to the maximum value recommended by the National Formulary of USP 21, January 1985, p. 971.

Advantageously, the concentration of sodium hypochlorite in the solution according to the invention will be between 4 and 5.5, preferably between 4.5 and 5.5 and even more preferably between 5.0 and 5.5.

The pH zone of the solution according to the invention is critical for obtaining a satisfactory efficacy/safety ratio.

The purified water used in the solution according to the invention must be an appropriate water for therapeutic use; for example, it will be possible to use the purified water corresponding to that described in the French Pharmacopeia, 10th edition, January 1989. Osmosed water will preferably be used as the purified water.

The solution according to the invention can also contain a coloring substance which is inert towards the sodium hypochlorite and the pH regulator. This coloring substance can be potassium permanganate, for example, as in DAKIN's solution.

The pH regulator used in the solution according to the invention is any type of agent which is inert towards the sodium hypochlorite and which makes it possible to adjust the pH of the solution to a value of between 10 and 10.5, preferably of about 10.25, without affecting the ciliary function, i.e. without affecting the tolerance with respect to the living cell in vitro.

Within the framework of the present invention, it is considered that the ciliary function is not affected when the cilia continue to beat for at least 60 minutes after application of the solution to ciliated cells, for example cells of living tracheal epithelium.

Examples which may be mentioned in particular of pH regulators which are appropriate for the purposes of the invention are monopotassium phosphate, dipotassium phosphate, monosodium phosphate or mixtures thereof, as well as buffer solutions which make it possible to obtain a pH of between 10 and 10.5 without affecting the ciliary function. Monosodium phosphate is very particularly preferred.

The solution according to the invention is a therapeutic solution which is stable for a period never achieved hitherto with DAKIN's solution, namely at least 24 months at 20°-25° C. Furthermore, the antiseptic and safety properties of this solution are superior or equal to those of the currently known solutions, as shown in the Comparative Examples below.

To demonstrate the advantages gained by using the solution according to the invention, said solution was compared with the solution described in patent FR 2 593 704.

These two solutions were prepared on the first day that the research protocols were started and the measurements made were as follows:
antiseptic activity;
tolerance with respect to the living cell (ciliary function);
physicochemical stability.

ANTISEPTIC ACTIVITY

The test for measuring this activity consists in bringing the test solutions into contact with reference germs in accordance with the dilution principle in order to determine the minimum inhibitory concentration which makes it possible to stop the microbial activity of the reference germs.

The investigations were carried out at the initial pH of the solutions and at two pH values within the pH range of the malpighian zones of application (pH 8.5 and 6.2).

The results obtained at the different pH values are shown in Table I below:

TABLE I

| | Antiseptic activity Minimum inhibitory concentration expressed in mg of active chlorine | | | | | |
|---|---|---|---|---|---|---|
| | at initial pH** | | at pH brought to 8.5* | | at pH brought to 6.2* | |
| | solution of the invention pH 10.25 | solution of patent FR 2 593 704 pH 9.8 | solution of the invention | solution of patent FR 2 593 704 | solution of the invention | solution of patent FR 2 593 704 |
| Pseudomonas aeruginosa | 0.38 | 0.87 | 0.54 | 0.87 | 0.49 | 0.87 |
| Escherichia coli | 0.54 | 0.87 | 0.54 | 0.97 | 0.49 | 0.87 |
| Staphylococcus | 0.49 | 0.87 | 0.49 | 0.97 | 0.49 | 0.87 |
| Streptococcus faecalis | 0.49 | 0.87 | 0.49 | 0.97 | 0.49 | 0.87 |
| Candida albicans | 0.49 | 0.87 | 0.49 | 0.87 | 0.38 | 0.68 |

*by the addition of hydrochloric acid
**The initial pH of the solutions corresponds to the median value of the range recommended in the present patent application or patent FR 2 593 704.

These results show that:

A—at the initial pH:

1) the efficacy of the solution according to the invention is greater than that of the solution of patent FR 2 593 704, whereas a reduction in activity might have been expected in the light of the teaching of the prior art [the journal Prescrire, July-August 1990, volume 10, No. 98];

2) it becomes possible to use a smaller amount of solution to obtain a comparable result in terms of antiseptic activity, whence the therapeutic value especially in the disinfection of chambers and cavities;

B—at different values (for example pH 8.5 and pH 6.2):

the solution according to the invention, which has a maximum pH of 10.5, retains a potential for generating nascent chlorine which is always greater than that of the solution of patent FR 2 593 704 (this is associated with the greater stability of this novel solution).

II. TOLERANCE WITH RESPECT TO THE LIVING CELL

The comparative study was performed on the ciliary function of living tracheal epithelium.

The value of verifying "in vitro" the integrity of the ciliary function under the influence of the two solutions is that it makes it possible to predict the possible safety of the two products "in vivo".

When the tests had been performed, it was possible to see that with the solution of the invention, the ciliary activity is integrally preserved throughout the duration of the tests, i.e. 60 minutes, with beating actions of comparable amplitude and intensity, whereas one might have expected a reduction in this function by the possible aggressiveness due to the alkalinity of the solution and the increase in the active principle content.

III. STABILITY

The stability with time of the solution of the invention, kept at 20°-25° C., was measured and compared with that of the solution according to patent FR 2 593 704 and DAKIN's solution.

The results obtained are reported in the single FIGURE attached, which shows the curves of the titer of active chlorine (ordinate) as a function of the time expressed in months (abscissa).

Curves 1 to 3 correspond respectively to:
curve 1: solution according to the invention,
curve 2: solution according to patent FR 2 593 704,
curve 3: DAKIN's solution.

Whereas the chlorometric titer of DAKIN's solution very quickly falls below the acceptable limit for therapeutic use (4 g/l) and that of the solution of patent FR 2 593 704 passes through this limit after about 18 months, the titer of the solution according to the invention is considerably above this limit for at least 24 months.

The solution according to the invention is therefore a stable solution which has an improved therapeutic efficacy compared with the solutions of the prior art.

What is claimed as:

1. A stable solution of sodium hypochlorite which contains:
   sodium hypochlorite in a quantity sufficient to yield 4 to 6 grams per liter of active chlorine;
   a pH regulator in a quantity sufficient for a pH greater than 10 and less than or equal to 10.5; and
   purified water in a quantity sufficient for 1 liter of said solution.
2. A solution according to claim 1 which contains from 4 to 5.5 grams per liter of active chlorine.
3. A solution according to claim 1 or claim 2 which contains from 4.5 to 5.5 grams per liter of active chlorine.
4. A solution according to claim 1 or claim 2 which contains from 5.0 to 5.5 grams per liter of active chlorine.
5. A solution according to claim 1 or claim 2, wherein the pH regulator is in a sufficient amount for a pH of 10.25.
6. A solution according to claim 1 or claim 2, wherein the pH regulator is selected from the group consisting of monosodium phosphate, monopotassium phosphate, dipotassium phosphate, mixtures thereof and buffer solutions.
7. A solution according to claim 1 or claim 2, wherein the pH regulator is monosodium phosphate.
8. A solution according to claim 1 or claim 2 which also contains potassium permanganate.

* * * * *